United States Patent [19]

Prendergast

[11] Patent Number: 4,956,355
[45] Date of Patent: Sep. 11, 1990

[54] AGENTS FOR THE ARREST AND THERAPY OF RETROVIRAL INFECTIONS

[75] Inventor: Patrick T. Prendergast, Baybush, Ireland

[73] Assignee: Colthurst Limited, Baybush, Ireland

[21] Appl. No.: 182,480

[22] Filed: Apr. 15, 1988

Related U.S. Application Data

[63] Continuation-in-part of Ser. No. 90,637, Aug. 27, 1987, abandoned.

[30] Foreign Application Priority Data

Apr. 16, 1987 [IE] Ireland ................................... 997/87
Aug. 27, 1987 [IE] Ireland ................................. 2289/87

[51] Int. Cl.$^5$ ..................... A61K 31/56; A61K 31/58; A61K 31/665; A61K 31/66
[52] U.S. Cl. ..................................... 514/178; 514/99; 514/102; 514/121; 514/172; 514/171
[58] Field of Search ................. 514/171, 172, 178, 99, 514/102, 121

[56] References Cited

U.S. PATENT DOCUMENTS

| | | | |
|---|---|---|---|
| 4,005,200 | 1/1977 | Utsumi et al. | 424/243 |
| 4,518,595 | 5/1985 | Coleman et al. | 514/178 |
| 4,602,008 | 7/1986 | Krsek | 514/178 |
| 4,628,052 | 12/1986 | Peat | 514/171 |
| 4,724,232 | 2/1988 | Rideout et al. | 514/50 |

FOREIGN PATENT DOCUMENTS 0133995 2/1984 European Pat. Off. .

OTHER PUBLICATIONS

The Merck Index, 10th ed. (1983); p. 1108; #7606 Prasterone.
Chemical Abstracts; vol. 100 (1984) #168,451e; Schwartz et al.
Crowe, et al., Quantitative Immunocytofluorographic Analysis . . . AIDS Research & Human Retroviruses, vol. 3, No. 2, 1987, pp. 135-145.
Henderson, et al., Dehydroepiandrosterone and 16α-bromo-epiandrosterone: Inhibitors of Epstein-Barr Virus-Induced Transformation of Human Lymphocytes, Carcinogenesis, vol. 2, No. 7, 1981, pp. 683-686.
Hidvegi, et al., Inhibition of the Complement Activation by an Adrenal Androgen, Dehydroepiandrosterone, Complement 1:201-206 (1984).
Ho, et al., Infection of Monocyte/Macrophages by Human T Lymphotropic Virus Type III, The American Society for Clinical Investigation, Inc., vol. 77, May 86, pp. 1712-1715.
Koo, et al., Effect of Dehydroepiandrosterone on Hereditary Angiodema, Klin Wochenschr, (1983) 61:715-717.
Lucas, et al., Prevention of Autoantibody Formation & Prolonged Survival in New Zealand . . . , The American Society of Clinical Investigations, Inc., vol. 75, Jun. 85, 2091-2093.

*Primary Examiner*—Joseph A. Lipovsky
*Attorney, Agent, or Firm*—Marla J. Church

[57] ABSTRACT

Compounds of the general Formula (I)

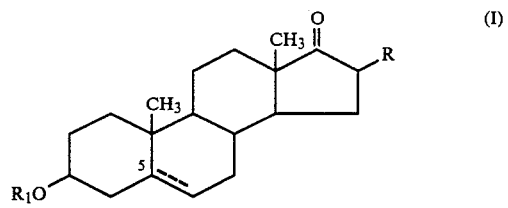

in which R is a hydrogen atom or a bromine atom, and $R_1$ is a hydrogen atom, an $SO_2OM$ group wherein M is a hydrogen or sodium atom, various sulphatide or phosphatide groups or a glucuronide group are disclosed for use in the prophylaxis and therapy of retroviral infections, especially infection by Human Immunodeficiency Virus. These compounds may be used concomitantly or in combination with various immunomodulators and/or antiviral agents.

16 Claims, 3 Drawing Sheets

AGENTS FOR THE ARREST AND THERAPY OF RETROVIRAL INFECTIONS

This case is a continuation-in-part of Ser. No. 07/090,637 Filed 8/27/87; now abandoned.

BACKGROUND OF THE INVENTION

The present invention relates to the use of certain 17-ketosteroids in the prophylaxis and therapy of retroviral infections or a complication or consequence thereof. In particular, the invention relates to the use of said 17-ketosteroids in the prophylaxis and therapy of retroviral infections leading to a deficiency of the immune system resulting in the development of opportunistic infections and certain cancers. More especially, the invention relates to the use of the 17-ketosteroids in the prophylaxis and therapy of retroviral infections thought to be responsible for the Acquired Immune Deficiency Syndrome (AIDS) and the related disease AIDS related complex (ARC). AIDS and ARC are believed to result from infection by the Human Immunodeficiency Virus (HIV) and antibodies to which are found in the serum of almost all persons diagnosed as suffering from AIDS or ARC. Lymphadenopathy-associated virus (LAV) and human T-lymphotrophic virus type III (HTLV-III), as well as related retroviruses have been isolated from a large number of AIDS patients. All of these viruses share important characteristics. HTLV-III and LAV are now believed to be strains of the same virus, which has been given the name Human Immunodeficiency Virus (HIV).

AIDS is a disease characterised by loss of cell-mediated immunity and the development of frequent and eventually fatal opportunistic infections. The diagnosis of AIDS is a clinical one, defined as "the occurrence of an illness predictive of a defect in cell-mediated immunity occurring in an individual with no known cause for diminished resistance to that disease" (Lane, H.C. & Fauci, A.S. Ann. Rev. Immunol. 1985, 3, 477–500).

The use of the term HIV embraces the retrovirus HIV-1 or HIV-2 (Human Immunodeficiency Virus Type 1 and Human Immunodeficiency Virus Type 2), which was discovered in 1983. HIV attacks and reduces the numbers of a subset of white blood cells known as T lymphocytes. Expressed on the cell surfaces of these T lymphocytes is a molecule known as CD4, (such cells are also known as T4 cells). Such lymphocytes, most of which are included in what is functionally defined as the helper/inducer subset, constitute the major proportion of mature T cells. Another major subset of T cells express the CD8 molecule on their cell surfaces (such cells are also known as T8 cells). Most of these are classified as suppressor/cytotoxic cells. Normally the T4/T8 ratio is 1.5 to 2.0. In AIDS patients, however, this ratio is inverted due to a decrease in the absolute numbers of T4 cells, with normal numbers of T8 cells usually being preserved.

T4 cells specifically recognise and proliferate in response to antigens that they encounter in the body, at the same time releasing a variety of proteins known as lymphokines that regulate other immune system cells. Upon signaling by T4 cells, B lymphocyte cells recognise antigens and secrete specific antibodies to neutralise or eliminate antigenic bacteria and viruses as they travel through body fluids between cells. Similarly, following signaling from T4 cells, cytotoxic T cells ("T8") become activated to kill cells infected with intracellular pathogens. Furthermore, T4 cells modulate the activities of immune system cells known as natural killer cells and macrophages, which are involved in response to infection and perhaps to incipient malignancies.

A critical and early event in HIV infection involves the virus' attachment, via its envelope glycoprotein, to a receptor on the surface of a susceptible T4 cell, the CD4 molecule. The CD4 molecule at the T4 cell surface appears to distinguish potential target cells from HIV and to act as the receptor molecule that binds the virus and allows infection and subsequent viral replication as well as the cytopathic consequences of viral infection.

The immunodeficiency of AIDS clearly demonstrates the importance of T4 lymphocytes. Because of the loss of these cells, the remaining T lymphocytes from AIDS patients have diminished or absent responses to antigens and show subnormal production of essential immuno-regulatory factors. Due to their decreased numbers and functional capacity, T4 cells are unable to fulfil their necessary role in providing direction for the maturation of B cells and cytotoxic T cells. The ability of AIDS patients to mount antibody reactions to new antigens is severely compromised, though paradoxically high levels of antibodies to previously encountered antigens, including HIV, are often present in patients' sera (Institute of Medicine, National Academy of Science, Confronting AIDS, Washington, D.C. National Academy Press 1986, pages 37–44 and 177–199).

At present AIDS and ARC are predominantly found in certain high risk groups such as homosexuals, intravenous drug abusers and those who have received multiple transfusions or products such as Factor VIII derived from blood. Blood donors are now routinely screened for antibodies to HIV and, therefore, future spread of HIV through blood transfusions and blood-derived products should not, hopefully, lead to transmission of AIDS. AIDS is also increasingly found in the heterosexual population.

There is increasing evidence that macrophage/monocyte infection is a vital factor in the persistence and progession of HIV infection, in initiating the brain damage that occurs in AIDS and in triggering the collapse of the immune system as evidenced by eventual profound depletion of T4 lymphocytes. Crowe et al. have demonstrated using anti-HIV p24 antibody that monocyte/macrophages can be infected with HIV. They have demonstrated that up to 70% of cells from individual donors could be infected (AIDS Research and Human Retroviruses, Vol. 3, No. 2, 1987, page 135). Nicholson et al. have proposed an HTLV-III/LAV-induced effect in monocyte function rather than (or in addition to) an intrinsic defect in surviving T cells to account for observed abnormalities in T cell assays that are monocyte-dependent such as pokeweed mitogen-induced Ig synthesis and proliferative responses to soluble antigens. These T cell assays have previously been reported as abnormal even when assayed as T cell subsets (The Journal of Immunology, Vol. 137, No. 1, 1986, page 323).

Since it is well established that the first event that occurs when a foreign material (for example, a virus) enters the body is its uptake by mononuclear phagocytes, it is conceivable that these cells represent a primary target for HIV. Gartner et al. have shown that virus production by HTLV-III/LAV infected macrophages was high and long-lived, indicating that these cells may play a role in virus dissemination and persistence. They have demonstrated HTLV-III/LAV replication in macrophages was fully productive in the situations they evaluated (Science Vol. 233, 1986, page 215).

Salahuddin et al. observed that in vitro pulmonary macrophages can be infected with HTLV-III and appear to be less susceptible to the phytopathic effects of this retrovirus which suggests that tissue macrophages should be considered as potential reservoirs of HTLV-III in vivo (Blood, Vol. 68, No.1, 1986, page 281).

Ho D.D. et al. observed normal blood-derived monocytes/macrophages were found to be susceptible to infection in vitro by human T Lymphotropic virus III (HTLV-III), the etiologic agent of the Acquired Immune Deficiency Syndrome. In addition, HTLV-III was recovered from monocytes/macrophages of patients infected with this virus. It was postulated therefore that HTLV-III-infected monocyte/macrophages may serve as a vehicle for the dissemination of virus to target organs and as a reservoir for viral persistence, as has been shown for other lentiviruses, including visna virus and caprine arthritis encephalitis virus (J. Clin. Invest., Vol. 77, 1986, page 1712).

While an antiviral agent which could kill all infecting HIV or completely inhibit its replication (and at the same time have an acceptable toxicity profile) is clearly desirable, the situation is that no such agent is at present available.

With the emerging understanding of the role that macrophages may be playing in the pathogenesis of AIDS, it is clear that an effective antiviral strategy will require an approach that can treat infected macrophages and inhibit infection of these cells. Currently the only F.D.A. approved antiviral agents for treatment of AIDS are azido thymidine (AZT) and pentamidine isethionate (PENTAM 300). As demonstrated hereinafter AZT is completely ineffective at inhibiting macrophage infection or modulating HIV production from infected macrophages. Administration of AZT over long periods of time has been found to give rise to undesirable side effects such as anaemia, necessitating blood transfusion, leucopenia and neutropenia.

The great majority of antiviral compounds are nucleosides, including, for example, AZT.

Many of the 17-ketosteroids function as hormones and include sex hormones or precursors thereof and hormones which control metabolism. Dehydroepiandrosterone (DHEA) is one such 17-ketosteroid which is a precursor of both androgens and estrogens and additionally has important metabolic effects. These effects ensue from its inhibitory effect on enzymes such as glucose-6-phosphate dehydrogenase and NADH oxidase. Additionally, DHEA has an inhibitory effect on mitotic activity and on the permeability of membranes (Jiri Sonka, Acta Universitatis Carolinae Medica Monographia LXXI -1976). The effect of DHEA on enzymes such as glucose-6-phosphate dehydrogenase and NADH oxidase leads above all to inhibition of the pentose cycle and of the cytochrome system, both of which restrict the supply of building materials and energy, necessary for biosynthetic processes, in particular for growth and regeneration of tissue. One of the main conditions of growth is an adequate supply of energy (ATP) and building materials for nucleic acid synthesis. DHEA controls both of these processes as an inhibitor of NADH oxidase and glucose-6-phosphate dehydrogenase. DHEA has been found to suppress some of the metabolic disorders and liver cirrhosis, and reduces pain in ischemic heart disease, especially in angina pectoris, by restricting tissue respiration. HEA has been used in the treatment of menopause, emotional instability, depression and stress.

Individuals who are genetically deficient in glucose-6-phosphate dehydrogenase are relatively resistant to Falciparum Malaria and have much smaller numbers of protozoa in their erythrocytes than normal individuals (Motulski, A.G. 1975, in "The Role of Natural Selection in Human Evolution", Ed. Salzano, S. Amsterdam, New Holland, P.271 and Luzzato, L. et al., Science, 164, 839, 1969).

DHEA and related compounds are capable of reducing the colony forming ability of human peripheral blood mononuclear (PBM) cells infected with Epstein-Barr virus (a herpes virus) at concentrations of 10-100 $\mu M$ (Carcinogenesis, Vol. 2, pp 883-886, 1981).

DHEA also inhibits complement activation and is therefore of value in the prophylaxis of Hereditary Angioneurotic Oedema (Hidvegi et al., Complement 1; 201, 1984). DHEA also prevents autoantibody formation in the murine model of Systemic Lupis Erythematosus (SLE) and many of the features of full-blown AIDS are considered to be similar to those of SLE (Lucas et al., J. Clin. Invest., 75: 2091, 1985).

SUMMARY OF THE INVENTION

According to the invention there is provided a compound for use in the prophylaxis and therapy of a retroviral infection, or a complication or consequence thereof, the compound having the general formula (I)

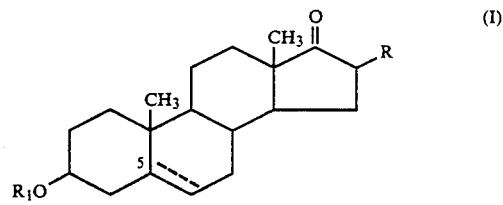

in which R is a hydrogen or bromine atom, and $R_1$ is a hydrogen atom, an $SO_2OM$ group wherein M is a hydrogen or sodium atom, a sulphatide group

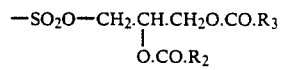

a phosphatide group

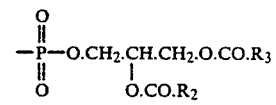

wherein each of $R_2$ and $R_3$, which may be the same or different, is a straight or branched chain alkyl radical of 1 to 14 carbon atoms, or a glucuronide group

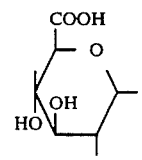

wherein the broken line represents an optional double bond, and the hydrogen atom at position 5 is present in the α- or β- configuration or the compound comprises a mixture of both configurations.

When $R_1$ is other than a hydrogen atom, the compounds are conjugated compounds.

Preferably in the compound of formula (I), R and $R_1$ are each hydrogen. An especially preferred compound is dehydroepiandrosterone wherein R and $R_1$ are each hydrogen and the double bond is present.

In a further embodiment of the invention, the compound is 16α-bromoepiandrosterone, wherein R is Br, $R_1$ is H and the double bond is present. In a still further embodiment of the invention, the compound is etiocholanolone wherein R and $R_1$ are each hydrogen and the double bond is absent.

Other preferred compounds are dehydroepiandrosterone sulphate, wherein R is H, $R_1$ is $SO_2.OM$ and M is as hereinbefore defined and the double bond is present, and 5β-androstan- 3β-ol-17-one.

Alternatively, the compound is selected from dehydroepiandrosterone sulphatides, phosphatides or glucuronide wherein R is H, and $R_1$ is a sulphatide, phosphatide or glucuronide group as hereinabove defined, and the double bond is present.

Additionally, the invention provides a pharmaceutical formulation for use in the prophylaxis and therapy of a retroviral infection or a complication or consequence thereof, comprising a prophylactically or therapeutically effective amount of at least one compound of the formula (I) as an active ingredient.

The pharmaceutical formulation according to the invention may be administered locally or systemically. By systemic administration is meant any mode or route of administration which results in effective levels of active ingredient appearing in the blood or at a site remote from the site of administration of said active ingredient.

The pharmaceutical formulation for systemic administration according to the invention may be formulated for enteral, parenteral or topical administration. Indeed, all three types of formulation may be used simultaneously to achieve systemic administration of the active ingredient.

Suitable formulations for oral administration include hard or soft gelatin capsules, dragees, pills, tablets, including coated tablets, elixrs, suspensions, syrups or inhalations and controlled release forms thereof.

Solid dosage forms in addition to those formulated for oral administration include rectal suppositories.

The compound of the formula (I) may also be administered in the form of an implant.

Suitable formulations for topical administration include creams, gels, jellies, mucilages, pastes and ointments. The compounds may also be formulated for transdermal administration, for example, in the form of transdermal patches so as to achieve systemic administration.

Suitable injectable solutions include intravenous, subcutaneous and intramuscular injectable solutions. The compound of the formula (I) may also be administered in the form of an infusion solution or as a nasal inhalation or spray.

The pharmaceutical formulation according to the invention is administered in unit doses comprising from to 1,000 mg of active ingredient. Preferably, each unit dose comprises from 50 to 500 mg of active ingredient.

According to one embodiment of the invention, the compound of formula (I) is administered at a rate of from 1 unit dose to 10 unit doses per day Administration of the compound of the formula (I) in accordance with the invention is continued for a period of at least five days and in certain cases may be given for the life of the individual.

Further, the invention provides use of a compound of the formula (I) in the manufacture of a medicament for use in the prophylaxis or therapy of a retroviral infection, or a complication or consequence thereof.

The invention also provides a method for treating a retroviral infection in a human or non-human patient, comprising administering a therapeutically effective amount of a pharmaceutical formulation comprising a compound of the formula (I) to said patient.

The invention further provides a method for the prophylaxis of a retroviral infection in a human or non-human patient, comprising administering a prophylactically effective amount of a pharmaceutical formulation comprising a compound of the formula (I) to said patient.

The compounds of the formula (I) hereinabove given and defined are particularly useful for the prophylaxis and therapy of infection by HIV, or a complication or consequence thereof.

According to a further aspect of the invention there is provided a method for the prophylaxis and therapy of Acquired Immunodeficiency Syndrome (AIDS) in a patient, which comprises administering to said patient a prophylactically or therapeutically effective amount of a compound of the formula (I) or a pharmaceutical formulation containing it.

According to a still further aspect of the invention, there is provided a method for the prophylaxis and therapy of Acquired Immunodeficiency Syndrome Related Complex (ARC) in a patient, which comprises administering to said patient a prophylactically or therapeutically effective amount of a compound of the formula (I) or a pharmaceutical formulation containing it.

The compounds of the formula (I) may also be used concomitantly or in combination with an immune system booster or immunomodulator as an agent in the prophylaxis and therapy of a retroviral infection, or a complication or consequence thereof. In this way the immunomodulator booster may be used to enhance the production of T-cells by the bone marrow.

The immunomodulator may be administered prior to and in an amount sufficient to stabilise or increase the production of T-cells prior to administering said compound of the formula (I). In particular, the immunomodulator is administered until the rate of production of T-4 cells is stabilised or begins to increase.

The compound of the formula (I) and the immunomodulator may be combined in a single dosage form or in discrete dosage forms.

Suitable immune system boosters or immunomodulators for use in accordance with the invention are selected from ABPP (Bropirimine); Ampligen (mismatched RNA) developed by Du Pont/HEM Research; anti-human α-Interferon antibody manufactured by Advance Biotherapy and Concepts; anti-AIDS antibody (Nisshon Food); AS-101 (heavy metal based immunostimulant), ascorbic acid and derivatives thereof; β-interferon; Carrosyn (polymannoacetate); Ciamexon manufactured by Boehringer Mannheim; Cyclosporin; Cimetidine; CL246,738 manufactured by American Cyanamid; colony stimulating factor (CM-CSF) manufactured by Sandoz and Genetics Institute; dinitrochlorobenzene (DNCB); α-interferon; γ-interferon; glucan; Hyperimmue (gamma-globulin) manufactured by Bayer; IMREG-1 (leucocyte dialyzate) and IMREG-2 manufactured by IMREG; immuthiol (sodium diethylthiocarbarmate) manufactured by Institut Merieux; Interleukin-1, Interleukin-2 manufactured by Cetus Corporation, Hoffmann-La Roche and Immunex; isoprinosine (inosine pranobex); Krestin manufactured by Sankyo; LC-9018 developed by Yakult; Lentinan manufactured by Ajinomoto/Yamanouchi; LF-1695 manufactured by Fournier; MET-ENK (methionine-enkephalin) manufactured by TNI Pharmaceuticals and Sygma Chemicals; Minophagen C; MTP-PE (muramyl tripeptide) manufactured by Ciba-Geigy; Trexan (Naltrexone) manufactured by Du Pont; Neutropin; RNA immunomodulator developed by Nippon Shingaku; shosaikoto and ginseng; thymic humoral factor; TP-5 (Thymopentin) manufactured by Ortho Pharmaceuticals; Thymosin fraction 5 and Thymosin 1; Thymostimulin; TNF (tumor necrosis factor) manufactured by Genentech; and vitamin B preparations.

The majority of the above mentioned immunomodulators are administered orally. Dinitrochlorobenzene is normally applied topically by painting onto the skin of the patient.

Accordingly, the invention also provides a pharmaceutical formulation comprising a compound of the formula (I) together with an effective amount of an immune system booster or immunomodulator.

The invention also provides a compound of the formula (I) for use concomitantly or in combination with an antiviral agent in the prophylaxis and therapy of a retroviral infection, or a complication or consequence thereof.

The compound of the formula (I) and the antiviral agent may be combined in a single dosage form or in discrete dosage forms.

Suitable antiviral agents include AL-721 (lipid mixture) manufactured by Ethigen Corporation and Matrix Research Laboratories; Amphotericin B methyl ester; Ampligen (mismatched RNA) developed by Du Pont/HEM Research; anti-AIDS antibody (Nisshon Food); AS-101 (heavy metal based immunostimulant); AZT (azidothymidine/Retrovir/Zidovudine) manufactured by Burroughs Wellcome; Betaseron (β-interferon) manufactured by Triton Biosciences (Shell Oil); butylated hydroxytoluene; Carrosyn (polymannoacetate) Castanospermine; Contracan (stearic acid derivative); Creme Pharmatex (contains benzalkonium chloride) manufactured by Pharmelac; CS-87 (5-unsubstituted derivative of Zidovudine); Cytovene (ganciclovir) manufactured by Syntex Corporation; DDC (dideoxycytidine) manufactured by Hoffmann-La Roche and other nucleoside analogues; dextran sulphate; D-penicillamine (3-mercapto-D-valine) manufactured by Carter-Wallis and Degussa Pharmaceutical; Foscarnet (trisodium phosphonoformate) manufactured by Astra AB; fusidic acid manufactured by Leo Lovens; glycyrrhizin (a constituent of liquorice root); HPA-23 (ammonium-21-tungsto-9-antimonate) manufactured by Rhone-Poulenc Sante; human immunevirus antiviral developed by Porton Products International; Ornidyl (eflornithine) manufactured by Merrell Dow; Nonoxinol; pentamidine isethionate (PENTAM 300) manufactured by Lypho Med; Peptide T (octapeptide sequence) manufactured by Peninsula Laboratories; Phenytoin marketed by Park-Davis (Warner-Lambert Company); Ribavirin; Rifabutin (ansamycin) manufactured by Adria Laboratories; rsT4 (recombinant soluble T4) manufactured by Biogen, Genentech and Smith Kline & French; Trimetrexate manufactured by Warner-Lambert Company; SK-818 (germanium-derived antiviral) manufactured by Sanwa Kagaku; suramin and analogues thereof manufactured by Miles Pharmaceuticals; UA001 manufactured by Ueno Fine Chemicals Industry; Wellferon (α-interferon) manufactured by Burroughs Wellcome; Zovirex (acyclovir) manufactured by Burroughs Wellcome.

It will be observed that the above mentioned antiviral agents include some of the agents hereinbefore specified for use as immunomodulators together with a compound of the formula (I) in accordance with the invention. Isoprinosine, for example, is known to act as an immunomodulator but also has antiviral properties. The term "antiviral" as used in the present Specification also include agents which interfere with the entry of retroviruses into a cell.

The invention may also provide a compound of the formula (I) for use concomitantly or in combination with a drug useful in the prophylaxis and therapy of AIDS-associated opportunistic infections.

As indicated hereinafter the compounds of formula (I) are particularly suitable for use as inhibitors of retroviruses, especially HIV, in macrophages.

EXAMPLES

Figure 1:
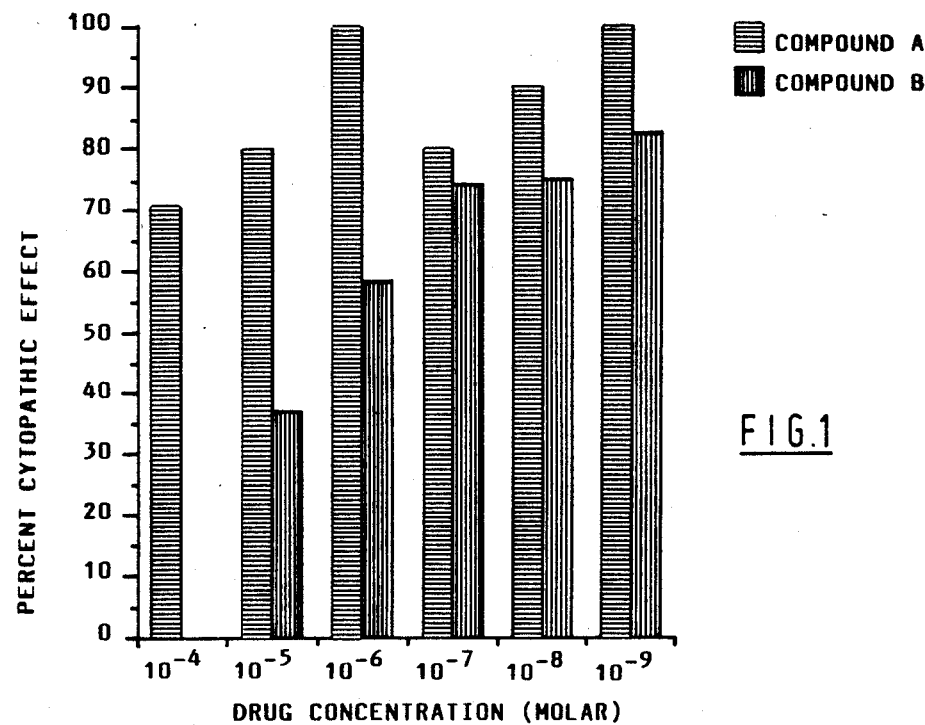
FIG. 1 is a schematic representation of percent cytopathic effect versus drug concentration in the VB tumor cell line for two compounds, designated A and B, used in accordance with the invention.

The invention will be further illustrated by the following Examples.

In the following Examples 1 to 7 compound A corresponds to dehydroepiandrosterone and compound B corresponds to 16α-bromoepiandrosterone.

In relation to Examples 1 to 7, the materials used and the analyses and assays carried out were as follows:

1. Source of HIV: To analyse antiviral effects in Examples 1 to 7 three substrains of HIV were used: the HTLV-IIIB strain of HIV, currently grown in tissue culture in the H9 cell line; the low passage isolate HIV-DV, a strain which has been shown to infect human macrophages; and the ARV-2 HIV strain first isolated by Dr. Jay Levy in San Francisco. All three viral strains were grown in the Tissue Culture Laboratory of the AIDS Activity Division of San Francisco General Hospital where titers of $10^{-4}$ to $10^{-6}$ infectious units per ml were routinely achieved.

2. Source of cells: The VB cell line used in Example 1 is a T lymphoma cell line that is highly susceptible to infection with HIV, and expresses high levels of cell surface CD4 molecules. This cell line forms syncytia within two days after infection with all strains of HIV tested to date. The H9 cell line is a T cell ALL that is susceptible to infection with virtually all strains of HIV, however, does not form syncytial cells. This is used to quantitate infection in the absence of syncytial formation, infection being quantitated by immunofluorescence assays. The HXB/H9 cell line (Example 6) is an H9 cell population that chronically produces the HTLV-IIIB strain of HIV and is utilised in experiments testing antiviral effects on chronically infected cell lines. Human macrophages were prepared from peripheral blood mononuclear cells either obtained from the blood bank as a buffy coat, or as a leukophoresis preparation. Crowe et al. supra have devised an assay system that allows quantitation of HIV infection, and inhibition of infection using immunocytofluorographic analysis. In order to quantitate HIV infection in macrophages, they grow macrophages in Teflon (Trade Mark) culture vessels which maintain macrophages in suspension in vitro culture for up to six months. Cell surface and cytoplasmic immunofluorescence staining is then performed to quantitate antigens in macrophages by flow cytometry.

3. Flow cytometry: An Ortho Cytofluorgraf II-S (Trade Mark) that has a biohazard containment flow cell was used for analysis of HIV infected samples. HIV p24 antigens were detected utilizing a mouse monoclonal anti-p24 (du Pont), and mouse antibodies were identified utilizing an FITC conjugated goat anti-mouse IgG.

4. HIV soluble p24 antigen detection: Soluble p24 antigens were measured with the Abbott HIV antigen detection system.

5. Inhibition of acute infection: Several assays were utilized to test for inhibition of acute infection; these included:

a) Inhibition of multinucleated giant cell formation in acutely infected VB cells infected at a multiplicity of infection of 1, and scored two days after infection in the presence or absence of varying concentrations of drug, for the formation of multinucleated giant cells. (free virus is washed out after a one hour incubation pretreatment at room temperature). Monoclonal antibody anti-Leu3a completely inhibits the formation of syncytial cells, and was utilized as a positive control for infection inhibition. Supernatants were also isolated and the level of HIV p24 antigen determined. Infectious virus was measured in treated cultures by performing a syncytial assay as described above.

b) Although the VB T lymphoma cell line behaves in a similar manner to peripheral blood CD4 positive T lymphocytes in regard to HIV induced cytopathic effects, the above described experiments were performed on phytohemagglutinin (PHA) activated lymphocytes to determine whether lymphocytes are more or less sensitive to Compounds A and B than is the VB cell line. In this assay system, at the time that multinucleated giant cells appeared within infected lymphocyte cultures, the supernatants were analyzed for the presence of HIV p24 antigens and were titered on indicator VB lymphoma cells to determine the titer of infectious virus present at each point.

c) To test whether Compounds A and B were effective at blocking acute infection of macrophages, macrophages from Teflon cultures were exposed at a multiplicity of 1 to HIV-DV in the presence or absence of various concentrations of drug (Examples 3-5). Normally, HIV expression peaks in human macrophages at approximately ten days after initial infection. Therefore, after infection for one hour at room temperature, followed by a wash and resuspension of the macrophages in various drug concentrations, macrophages were stained for the presence of p24 antigen at day ten. Culture supernatants from these macrophages were assayed for the presence of soluble p24, and infectious virus as described above.

6. Analysis of chronically infected cells: To determine whether compounds A and B are effective at inhibiting HIV expression in macrophages and chronically infected T cells, the following experiments were performed. The chronically infected T cell line, HXB/H9 was exposed to various concentrations of drug for four days in vitro. At four days, the HXB cells were assayed for the presence of p24 intracytoplasmically, and supernatants were assayed for the presence of infectious virus as described above. These same experiments were performed on macrophages that had been infected in vitro and had been shown to be chronically infected by cytofluorographic analysis.

7. Analysis of nonspecific toxicity to the target cells with Compounds A and B. The VB, H9 and HXB cell lines were exposed to different concentrations of Compounds A and B as were normal human macrophages for the length of time the drug was in contact with each cell line as described in the above assays. Cell numbers were counted, and live versus dead were determined by Trypan blue exclusion assays. These tests were required to determine a therapeutic index between nonspecific toxic effects on the described cells, compared with potential effective antiviral effects in vitro (Example 6).

EXAMPLE 1

Inhibition of HIV mediated cytopathic effects in the VB tumor cell line

Compounds A and B were tested for inhibition of T lymphoma cell cytopathic effect at various drug concentrations after acute infection with HIV for 48 hours. FIG. 1 indicates the percent cytopathic effect observed in cultures exposed to various concentrations of compounds A and B. It will be observed that compound B appears to be more active at inhibiting HIV mediated multinucleated syncytial cell formation than compound A. The values for cytopathic effect shown in FIG. 1 were obtained for an average of two experiments. Two subsequent experiments utilizing compounds A and B that had been diluted in dimethyl sulphoxide (DMSO) revealed a less striking effect. It is possible that the diminished effects noted in later experiments could have been secondary to drug stability problems. At $10^{-4}$ molar compound B appeared to be extremely toxic to the VB T lymphoma cell line, a characteristic not shared by either the normal peripheral blood lymphocytes or macrophages exposed to $10^{-4}$ molar compound B, as hereinafter indicated in Examples 2 and 3, respectively.

EXAMPLE 2

Figure 2:
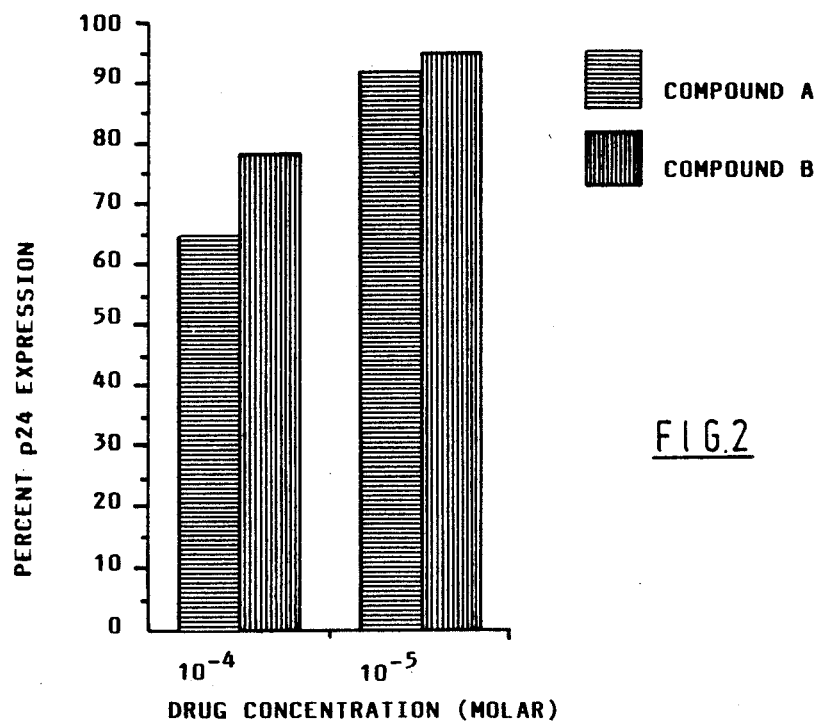
FIG. 2 is a schematic representation of percent p24 expression versus drug concentration in activated peripheral blood lymphocytes for two compounds, designated A and B, used in accordance with the invention.

Inhibition of HIV mediated cytophatic effects in activated peripheral blood lymphocytes To test whether the effects of compounds A and B on acute VB T lymphoma infection would be mimicked by activated peripheral blood lymphocytes (PBC), HIV at a multiplicity of infection of one was added to lymphocytes that had been activated for 48 hours with 2 µg per ml of PHA. After the initial infection for one hour, the activated lymphocytes were washed and resuspended for the on week of culture. Multinucleated giant cells began to form approximately 7 days after the initial infection, at which time the culture supernatants were harvested and tested for the presence of HIV p24 antigens. The accumulation of HIV p24 antigens in the supernatant is representative of production of HIV from infected cells. It will be noted from FIG. 2 that p24 antigen production was moderately inhibited at $10^{-4}$ molar with both compounds A and B and was slightly less inhibited at $10^{-5}$ molar. No appreciable toxicity was noticed at either drug concentration with the PBL cultures.

EXAMPLE 3

Inhibition of HIV production in normal human macrophages

Figure 3:
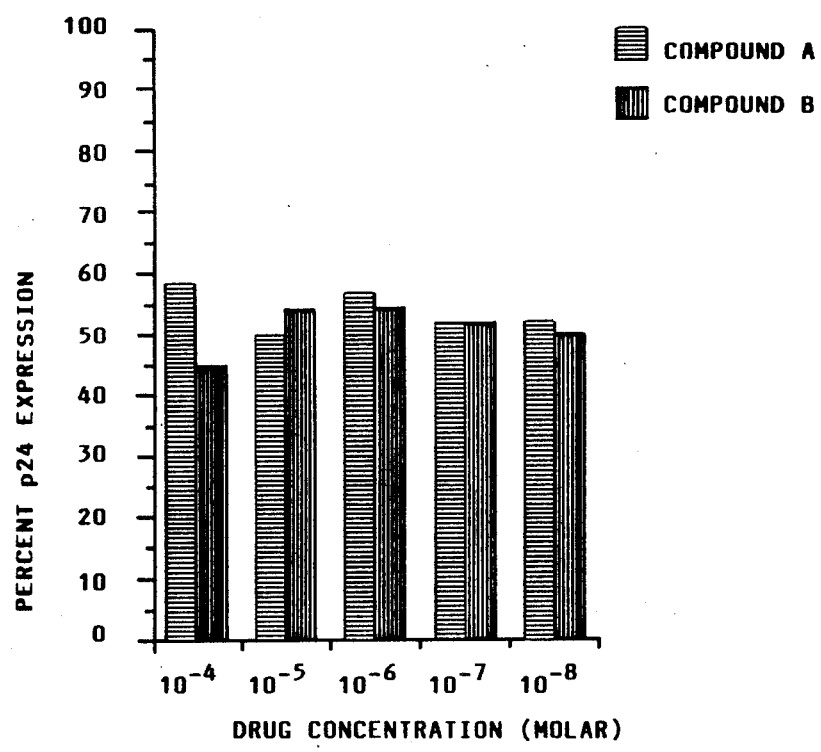
FIG. 3 is a schematic representation of percent p24 expression versus drug concentration in human macrophages for two compounds, designated A and B, used in accordance with the invention.

To test whether compounds A and B might be active at inhibiting infection of normal human macrophages, a spectrum of drug concentrations were tested for inhibition of acute infection, and inhibition of HIV expression in chronically infected macrophages. FIG. 3 indicates the presence of HIV p24 antigens in the supernatant of macrophages infected, washed and allowed to become productively infected for one week. After acute infection (one hour) cells were incubated in various concentrations of compounds A and B, and 7 days after the initial infection supernatants were harvested for p24 antigen quantitation. It will be observed that over a very broad range of drug concentration ($10^{-4}$ through $10^{-8}$ molar) there appeared to be a substantial, approximately 50% decrease in production of HIV p24 antigens. Macrophages treated with DMSO (at $10^{-4}$ molar drug concentration the final DMSO concentration was 0.05%) at concentrations required to dissolve compounds A and B showed no effect, therefore, these effects were apparently secondary to actions of compounds A and B.

EXAMPLE 4

Inhibition of HIV p24 antigen in HIV-infected macrophages

Figure 4:
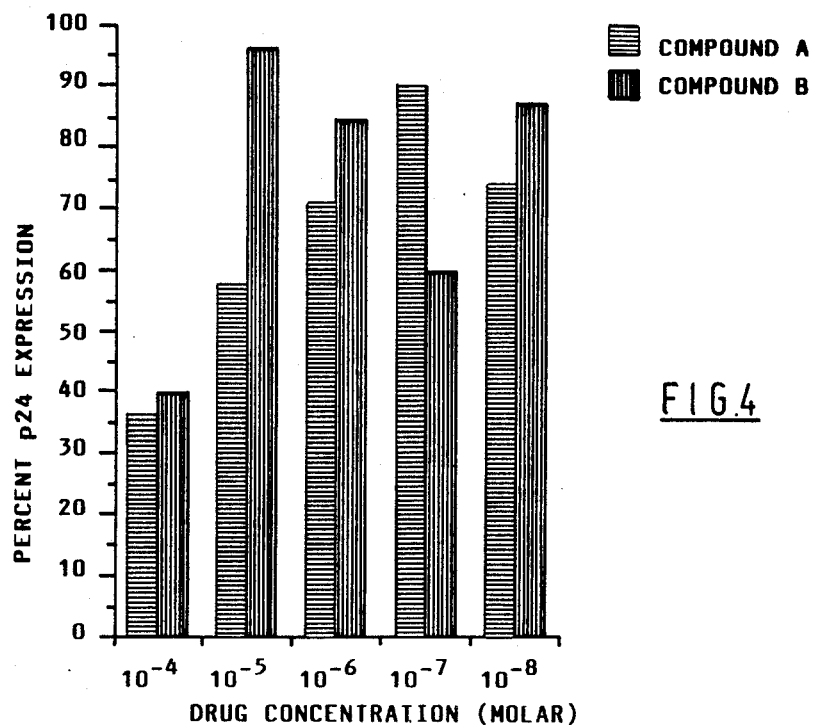
FIG. 4 is a schematic representation of percent p24 expression versus drug concentration in HIV infected macrophages for two compounds, designated A and B, used in accordance with the invention.

The cells from the experiment described in Example 3 were analysed, and the cytoplasm was analysed for the presence of HIV p24 to directly test whether HIV p24 antigen production was inhibited within those infected cells. FIG. 4 indicates a composite of three separate experiments utilizing infected macrophages from three different donors. It will be observed that HIV p24 cytoplasmic antigen production was substantially inhibited at $10^{-4}$ molar with both drugs, and that compound A was active at dilutions even at $10^{-6}$ molar in inhibiting HIV p24 antigen production within infected macrophages. Therefore, the decrease in HIV p24 within infected supernatants appeared to be associated with decreased HIV p24 antigen production within the infected macrophages.

EXAMPLE 5 (COMPARISON)

The same experiments described in Example 4 were repeated with AZT, at concentrations from 0.05 µg per ml to 50 µg per ml with no change from control values. Accordingly, the inhibition of HIV p24 antigen appeared to be specific at least in this test, for compounds A and B and was not a characteristic of AZT even at very high doses.

EXAMPLE 6

Antiviral testing of chronically HIV infected cell line, HXB

Chronically HIV infected cell line, HXB was tested with compounds A and B for antiviral effects, and other than killing with compound B at concentrations of $10^{-4}$ molar there appeared to be no specific inhibition of HIV production of cytopathic effects in the chronically infected lymphoma cell line.

EXAMPLE 7

Antiviral testing of chronically HIV infected macrophages

Figure 5:
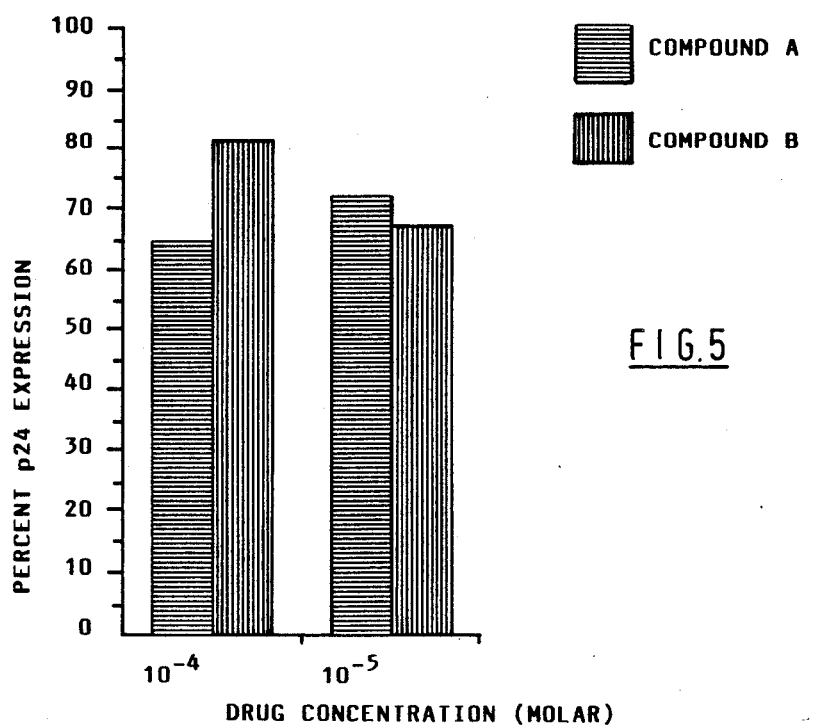
FIG. 5 is a schematic representation of percent p24 expression versus drug concentration for chronically infected human macrophages for two compounds, designated A and B, used in accordance with the invention.

Because macrophages can be infected and produce HIV for very long periods of time without substantial loss of viability, chronically infected cells were tested, specifically a population that was between 30 and 50% HIV antigen positive, for inhibition of cytoplasmic HIV p24 antigen production. FIG. 5 indicates the results of three separate experiments carried out. It will be observed there was some inhibition of HIV p24 antigen production at both $10^{-4}$ and $10^{-5}$ molar of compounds A and B, although somewhat less than the inhibition of acute infection of macrophages (FIG. 4). These data suggest that stably infected and chronically producing macrophages may be somewhat inhibited in their HIV p24 antigen production in the presence of compound A and B. Toxicity studies In all of the experiments described in Examples 1 to 7, the only appreciable toxicity was to tumor cell lines by compound B at $10^{-4}$ molar. There was not appreciable toxicity in normal macrophages exposed to $10^{-4}$ to $10^{-8}$ molar compounds A and B, nor was there appreciable toxicity to peripheral blood lymphocytes exposed to those same levels of drug.

Conclusions

The data presented in Examples 1 to 7, above, are consistent with the following interpretations.

1. Compounds A and B appear to exert a mild antiviral effect in acute infection studies of both T lymphoma cells as well as lymphocytes. In comparison with AZT, compounds A and B are inferior in terms of their antiviral effects, as AZT gives virtually complete protection of both lymphocytes and the T lymphoma cells from acute infection with HIV (as measured at one week) in the range of 1 µg of AZT per ml of culture medium.

2. Of more significance than the antiviral effect noted on the T lymphoma cell line and the peripheral blood lymphocytes were the observed effects of compounds A and B on HIV infection of macrophages. The results obtained in Examples 3-7 are significant, certainly at the level of in vitro inhibition of HIV infection of macrophages and inhibition of macrophage production of HIV. These were reproducible findings that were repeated with six separate monocyte/macrophage donors. Inhibition of HIV infection of macrophage is to date a relatively unique characteristic for an antiviral agent. The fact that compounds A and B inhibit HIV infection and HIV expression in macrophages suggest that they should prove useful for the treatment of HIV infected individuals.

EXAMPLE 8

Use of dehydroepiandrosterone sulphate in AIDS therapy

Dehydroepiandrosterone sulphate was measured into unit doses of 300 mg and 100 mg and each unit dose enclosed in a soft gelatin capsule.

A) A patient sero positive for HIV and diagnosed as suffering from AIDS was treated as follows. For twelve consecutive days, the patient was treated by administering the encapsulated compound orally to the patient. For the first eleven days, a unit dose of 300 mg was administered, once per day. On the twelfth day, the patient was given a single unit dose of 100 mg of the compound.

B) Trials were carried out over a twenty-six day period on two patients sero positive for HIV and diagnosed as suffering from AIDS using the twelve day treatment method discussed in the preceding paragraph except that treatment did not commence until day 5.

Blood samples were taken from the patients on five occasions over the twenty-six day period. The first tests were carried out on each patient on day 1 and included measurements of T1, T4 and T8 cell counts, as well as, sedimentation rate. The treatment commenced on day 5, and continued to day 17. From day 5 to day 16, each patient, as already discussed, received a single unit dose of 300 mg of dehydroepiandrosterone sulphate orally and on day 17 100 mg was administered. The aforementioned tests were repeated on each patient on day 9, day 17, day 24 and day 26. The T4 cell count in each of patients X and Y was found to stabilise as a result of the treatment.

Additionally, while the dehydroepiandrosterone sulphate was being administered orally to the patients, lesions around their mouth and on other parts of their body were treated topically with a cream containing dehydroepiandrosterone sulphate. It was found that the lesions cleared up.

EXAMPLE 9

Use of dehydroepiandrosterone in AIDS therapy

Twelve patients all of whom were sero-positive for HIV and had been diagnosed as suffering from AIDS were treated with DHEA for up to six months. The DHEA was administered in the form of hard gelatin capsules containing 100 mg of DHEA and at a rate of 100 mg to 600 mg per day. The vast majority being on 500 mg per day in divided doses. The patients were all homosexual or bisexual males with an average age of 34.5 years and an average weight of 69.6 kg.

Past and present HIV clinical manifestations included: unexplained diarrhoea, Kaposis Sarcoma, Herpes Zoster, Oral Candidiasis, Lymphadenopathy, Oral Hairy Leucoplakia, involuntary weight loss, dermal mycoses and Stapholococcal skin infections.

All of the patients were in an advanced stage of AIDS at the commencement of the trial and normally further deterioration of their condition, or even death, would have been expected over the six month period of the trial. However, no serious deterioration in condition was observed in any of the patients, with four patients actually gaining weight. Patient 7 gained 8 kg over five months.

Compounds of the formula (I) and, in particular, dehydroepiandrosterone and the derivatives thereof hereinbefore mentioned have particular advantages in the treatment of patients infected with HIV. Particular advantages of such compounds include the virtual absence of toxicity, ease of administration and the unique action on the macrophage system referred to above.

Dehydroepiandrosterone has demonstrated a complete lack of adverse physical, biochemical or hematological effects in twelve subjects who received daily doses of up to 600 mg for up to six months.

Because of the unique action of dehydroepiandrosterone in the macrophage system, it is possible that use thereof could extend the mean survival time of HIV infected individuals, which is calculated at present to be 8.3 years from the time of infection.

Furthermore, compounds of the formula (I) can be used in synergistic combination with other antiviral agents as indicated above.

Although not wishing to be bound by any theoretical explanation of the invention it is postulated that since dehydroepiandrosterone inhibits glucose-6-phosphate dehydrogenase leading to a depletion of the cellular pool of NADPH, resulting small changes of protein biosynthesis in the cell may, because of the complex regulation of HIV gene expression, lead to significant changes in viral protein production. An example of such a viral regulatory protein is art/trs which is present in very small amounts in infected cells, but is responsible for regulating viral RNA splicing and, consequently, viral protein production.

I claim:

1. "A method for treating or arresting the progression of a retroviral infection in a patient in need of such treatment which comprises administering to said patent A". therapeutically effective amount of a compound of the formula (I).

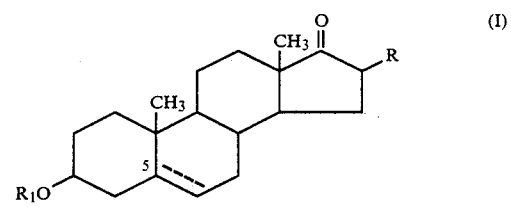

in which R is selected from the group consisting of a hydrogen atom and a bromine atom, and $R_1$ is a chemical group selected from the group consisting of a hydrogen atom, an $SO_2OM$ group wherein M is selected from the group consisting of a hydrogen atom, a sodium atom, a sulphatide group

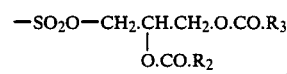

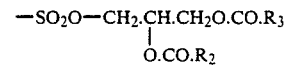

wherein each of $R_2$ and $R_3$, which may be the same or different, is selected from the group consisting of straight and branched chain alkyl radicals of 1 to 14 carbon atoms, a phosphatide group

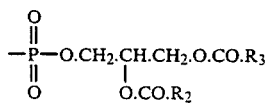

wherein each of $R_2$ and $R_3$, which may be the same or different, is selected from the group consisting of straight and branched chain alkyl radicals of 1 to 14 carbon atoms, and a glucoronide group

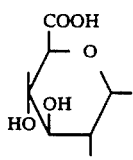

wherein the broken line represents an optical double bond, and the hydrogen atom at position 5 is present in the α- or β-configuration or a mixture of both configurations.

2. A method according to claim wherein in the compound of the formula (I) R and $R_1$ are each hydrogen.

3. A method according to claim 2, wherein the compound is dehydroepiandrosterone, the compound wherein R and $R_1$ are each hydrogen and the double bond is present.

4. A method according to claim 1, wherein the compound is 16α-bromoepiandrosterone, the compound wherein R is bromine, $R_1$ is hydrogen and the double bond is present.

5. A method according to claim 1, wherein the compound is dehydroepiandrosterone sulphate.

6. A method according to claim 1, wherein the compound of formula (I) is formulated for systemic administration.

7. A method according to claim 1, wherein the compound of the formula (I) is administered concomitantly or in combination with an immunomodulator.

8. A method according to claim 1, wherein the compound of the general formula (I) is administered concomitantly or in combination with an antiviral agent.

9. "A method according to claim 1 wherein the retroviral infection is a HUman Immunodeficiency Virus Infection".

10. "A method according to claim 1 wherein the retroviral infection has progressed to Acquired Immunodeficiency Syndrome (AIDS)."

11. A method according to claim 10, wherein the compound of the Formula (I) is administered concomitantly, or in combination with an immunomodulator.

12. A method according to claim 10, wherein the compound of the Formula (I) is administered concomitantly or in combination with an antiviral agent.

13. "A method according to claim 1 wherein the retroviral infection has progressed to Acquired Immunodeficiency Syndrome Related Complex (ARC).

14. A method according to claim 13, wherein the compound of Formula (I) is administered concomitantly or in combination with an immunomodulator.

15. A method according to claim 13, wherein the compound of the Formula (I) is administered concomitantly or in combination with an antiviral agent.

16. A method for the treatment of a patient who has a retroviral infection, which comprises administering to said patient a prophylactically or therapeutically effective amount of a compound of the formula (I)

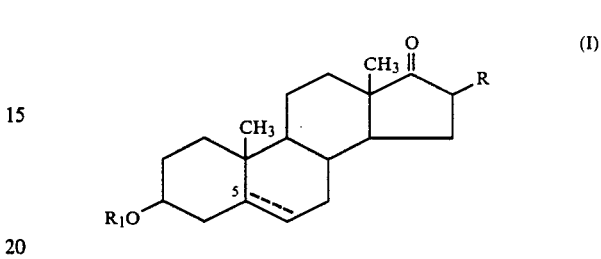

in which R is selected from the group consisting of a hydrogen atom and a bromine atom, and $R_1$ is a chemical group selected from the group consisting of a hydrogen atom, an $SO_2OM$ group wherein M is selected from the group consisting of a hydrogen atom, a sodium atom, a sulphatide group

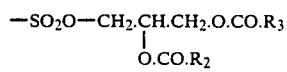

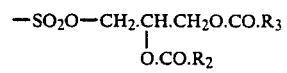

wherein each of $R_2$ and $R_3$, which may be the same or different, is selected from the group consisting of straight and branched chain alkyl radicals of 1 to 14 carbon atoms, a phosphatide group

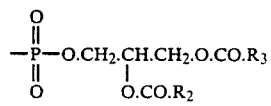

wherein each of $R_2$ and $R_3$, which may be the same or different, is selected from the group consisting of straight and branched chain alkyl radicals of 1 to 14 carbon atoms, and a glucuronide group

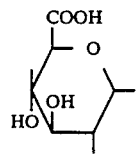

wherein the broken line represents an optical double bond, and the hydrogen atom at position 5 is present in the α-or β- configuration or a mixture of both configurations.—

* * * * *